United States Patent
Bernardi et al.

(10) Patent No.: US 10,006,072 B2
(45) Date of Patent: Jun. 26, 2018

(54) METHOD FOR MEASURING RESISTANCE OF BIOFILMS

(75) Inventors: Thierry Bernardi, Perignat les Sarlieve (FR); Pascal Mayer, Marsat (FR); Jerome Groelly, Beaumont (FR)

(73) Assignee: BIOFILM CONTROL, Saint Beauzire (FR)

( * ) Notice: Subject to any disclaimer, the term of this patent is extended or adjusted under 35 U.S.C. 154(b) by 168 days.

(21) Appl. No.: 13/996,960

(22) PCT Filed: Dec. 21, 2011

(86) PCT No.: PCT/FR2011/053138
§ 371 (c)(1),
(2), (4) Date: Sep. 11, 2013

(87) PCT Pub. No.: WO2012/085468
PCT Pub. Date: Jun. 28, 2012

(65) Prior Publication Data
US 2014/0051108 A1 Feb. 20, 2014

(30) Foreign Application Priority Data
Dec. 21, 2011 (FR) .................................. 10 60960

(51) Int. Cl.
*C12Q 1/02* (2006.01)
(52) U.S. Cl.
CPC ............... *C12Q 1/02* (2013.01); *C12Q 1/025* (2013.01)
(58) Field of Classification Search
CPC ...................................................... C12Q 1/02
See application file for complete search history.

(56) References Cited

U.S. PATENT DOCUMENTS

2008/0038769 A1\* 2/2008 Bernardi ................ G01N 11/10
435/29

FOREIGN PATENT DOCUMENTS

FR 2 916 761 12/2008

OTHER PUBLICATIONS

Chavant, et al., "A new device for rapid evaluation of biofilm formation potential by bacteria", *Journal of Microbiological Methods*, 68(3):605-612 (2007).
Larson, et al., "Surface adhesion measurements in aquatice biofilms using magnetic particle induction; MagPI", *Limnology and Oceanography: Methods*, 7:490-497 (2009).
Singh, "Refractive index measurement and its applications", *Physica Scripta*, 65:167-180 (2002).
Voros, et al., "The density and refractive index of adsorbing protein layers", *Biophysical Journal*, 87(1):553-561 (2004).

\* cited by examiner

*Primary Examiner* — Ruth A Davis
(74) *Attorney, Agent, or Firm* — Baker Botts L.L.P.

(57) ABSTRACT

The present invention relates to a method for measuring the effect of a force on a film. In particular, the present invention relates to a method for measuring the effect of a mechanical, hydrodynamic or physical force, for example, on the integrity of a film, for example a film made of microorganisms, foodstuffs and/or chemical substances. The present invention is especially applicable to the fields of biology, chemistry, biotechnology and food processing.

11 Claims, 9 Drawing Sheets

METHOD FOR MEASURING RESISTANCE OF BIOFILMS

TECHNICAL FIELD

The present invention relates to a process for measuring the impact of an action on a film. In particular, the present invention relates to a process for measuring the effect of an action, for example a mechanical, hydrodynamic, physical, chemical or biological action, on the integrity of a film.

The present invention especially finds an application in the field of biology, chemistry and biotechnology.

In the description below, the references between brackets ([Ref.]) refer to the list of references presented at the end of the text.

PRIOR ART

There are a multitude of deposits or thin layers of inert or living (biological) substances bound to supports: for example paints, varnishes, films composed of macromolecules, biofilms of microorganisms and various cells, for example bacteria, yeasts, algae, and cells of multicellular organisms. In what follows, these layers and deposits on a support will be denoted by the term "film".

Among these films, a large number form gradually over time, for example by polymerization of monomers, by aggregation or interpenetration of macromolecules, by growth of biofilms of microorganisms, by cell multiplication and/or production of substances binding the cells to one another.

This formation may often be adjusted by various physical parameters or substances, the impact of which it is useful to know. A film may also be modified after its formation by the action of a physicochemical treatment, for example by detergents, solvents, radiation, for example heat action, etc.

All these actions may result in films for which it may be interesting to know the resistance to a hydrodynamic action, such as a jet, a stream or the shaking of a solution which covers the film. For example, it is also possible to simply be interested in knowing whether this film has still been able to form or whether it has been broken up. In the remainder of this document these properties will be denoted by the term "integrity".

Known processes make it possible to compare the integrity of films of various natures, obtained by various methods of formation and resulting from various treatments.

For example, in one of the known processes, a support, the color of which is different from that of the film, is used. Thus, when the films are formed on this support, it is easy for a person skilled in the art to measure the integrity thereof after, for example a hydrodynamic action, a physicochemical treatment and/or an adjustment of its formation by analysis of an acquired image.

However, there are also films that are transparent or that cannot be colored, for example living films, films formed by microorganisms, films resulting from polymerization or aggregation for which the substance used for the coloring may interfere with their formation.

Processes exist in the prior art in order to measure the integrity of a film from, for example, its physical properties, such as its refractive index, for example in Singh et al., Physica Scripta. Vol. 65, 167-180 (2002): "Refractive Index Measurement and its Applications" [Ref. 1] and in Vörös et al. Biophysical Journal, Vol. 87, 553-561 (2004): "The Density and Refractive Index of Adsorbing Protein Layers" [Ref. 2].

However, these processes are expensive processes that require training and qualified staff and also sophisticated and expensive instruments.

There are situations, for example in the medical field or the biological field, where it is necessary to measure the integrity of a large number of different films in the presence of chemical compounds, biological molecules, thermodynamic modifications, etc. It may be a question, for example, of evaluating the effectiveness of a compound on biofilms or else the action, for example the degradation, modification or effectiveness, of an enzyme on a polymer film.

In these situations, for example on the occasion of screening runs for molecules or enzymes that are active against biofilms, for example for assessing the effectiveness of antibiotics on biofilms within the context of medical care, the techniques described previously are not satisfactory since they do not enable a person skilled in the art to carry out the measurements at a fast enough rate.

Moreover, the known processes require the use of a large number of instruments which cannot be used simultaneously in a screening process. Furthermore, the instruments used are expensive, and require the presence of qualified staff.

Moreover, the time for obtaining the results with the known processes is very long and may require the addition of reactants that are capable of modifying the result and therefore of leading to a variability of the results and the lack of reproducibility thereof.

There is therefore a real need to find a process for measuring the effect of an action on a film that overcomes these failings, drawbacks and obstacles of the prior art, in particular a process that makes it possible to control the time, to reduce the instrumentation necessary for this process, to reduce the costs and to improve the detection of the effect.

DESCRIPTION OF THE INVENTION

The process of the present invention makes it possible to resolve the aforementioned failings, drawbacks and obstacles of the prior art.

In particular, one subject of the present invention is a process for measuring the effect of at least one action on a film comprising the following steps:

a. introducing, into a solution, at least one substance capable of forming a film,
b. introducing, into the solution obtained in (a), at least two particles, said particles resting on a submerged surface S in said solution,
c. regrouping of the particles on said submerged surface S, said particles forming on said surface a spot or a mark,
d. forming said film from said substance,
e. observing the spot or mark on the surface S,
f. applying a mechanical and/or physical action to said solution,
g. observing the effect on the film of the action applied in step (e) by observing the spot or mark on the surface S, and
h. determining the effect of the action applied to the film by comparing the observations from the aforementioned steps (e) and (g).

According to the invention, a substance capable of forming a film may be, for example, microorganisms, foodstuffs, chemical substances, synthetic macromolecules, biological macromolecules, colloids and emulsions, objects of microscopic size and objects of nanoscopic size.

These may be, for example, eukaryotic cells, for example animal eukaryotic cells, for example blood cells, for example leukocytes, for example granulocytes, neutrophilic leukocytes; eosinophilic leukocytes; basophilic leukocytes; B lymphocytes, T lymphocytes, NK lymphocytes, monocytes, erythrocytes, thrombocytes. They may also be plant eukaryotic cells, for example plant epidermal cells, xylem cells, phloem cells, parenchyma cells, collenchyma cells and sclerenchyma cells. They may also be fungi or yeasts. They may be, for example, *Candida, Cryptococcus, Malassezia, Pityrosporum, Pneumocystis, Epidermophyton, Microsporum, Trichophyton*. They may also be protozoa, for example *Entamoeba histolytica, Acanthamoeba castellanii, Naegleria fowleri*.

They may also be prokaryotic cells, for example any bacterium known to a person skilled in the art, for example the bacteria included in the group, without being limited thereto, consisting of *Acetobacter aurantius, Actinobacillus actinomycetemcomitans, Agrobacterium tumefaciens, Azorhizobium caulinodans, Azotobacter vinelandii, Bacillus anthracis, Bacillus brevis, Bacillus cereus, Bacillus fusiformis, Bacillus licheniformis, Bacillus megaterium, Bacillus stearothermophilus, Bacillus subtilis, Bacteroides gingivalis, Bacteroides melaminogenicus, Bartonella henselae, Bartonella quintana, Bordetella bronchiseptica, Bordetella pertussis, Borrelia burgdorferi, Branhamella catarrhalis, Brucella abortus, Brucella melitensis, Brucella suis, Burkholderia mallei, Burkholderia pseudomallei, Calymmatobacterium granulomatis, Campylobacter coli, Campylobacter jejuni, Campylobacter pylori, Chlamydia pneumoniae, Chlamydia psittaci, Chlamydia trachomatis, Chlamydophila pneumoniae, Chlamydophila psittaci, Clostridium botulinum, Clostridium difficile, Clostridium perfringens, Clostridium tetani, Clostridium welchii, Corynebacterium diphtheriae, Corynebacterium fusiforme, Coxiella burnetii, Ehrlichia chaffeensis, Enterococcus avium, Enterococcus durans, Enterococcus faecalis, Enterococcus faecium, Enterococcus gallinarum, Enterococcus maloratus, Escherichia coli, Francisella tularensis, Fusobacterium nucleatum, Gardnerella vaginalis, Haemophilus ducreyi, Haemophilus influenza, Haemophilus parainfluenzae, Haemophilus pertussis, Haemophilus vaginalis, Helobacter pylori, Klebsiella pneumoniae, Klebseilla rhinoscleromatis, Klebsiella oxytoca, Lactobacillus acidophilus, Lactobacillus casei, Lactococcus lactis, Legionella pneumophila, Methanobacterium extroquens, Microbacterium multiforme, Micrococcus luteus, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma pneumonia, Neisseria gonorrhoeae, Neisseria meningitidis, Nocardia asteroids, Pasteurella multocida, Pasteurella tularensis, Porphyromonas gingivalis, Pseudomonas aeruginosa, Pseudomonas maltophilia, Rhizobium radiobacter, Rickettsia prowazekii, Rickettsia mooseri, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Staphylococcus aureus, Staphylococcus epidermidis, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactic, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema pallidum, Vibrio cholera, Vibrio comma, Vibrio parahemolyticus, Vibrio vulnificus, Xanthomonas maltophilia, Yersinia enterocolitica, Yersinia pestis and Yersinia pseudotuberculosis*, etc.

The expression "colloids and emulsions" is understood to mean a substance in liquid or semi-solid form which contains small enough particles for the mixture to be homogeneous. It may be any colloid and emulsion known to the person skilled in the art. It may be, for example, any substance and/or composition comprising two distinct phases. It may be, for example, a liquid containing, in suspension, particles, for example liposomes, droplets, aggregates, which may have a particle size for example from 2 to 200 nanometers, for example from 201 nm to 5 µm. It may be, for example, nanoemulsions, milk, milk cream, butter, mayonnaise, moisturizing cream, clays, colloidal gold or colloidal silver, and oil-in-water, ferrofluid-in-water and water-in-oil synthetic emulsions.

According to the invention, the expression "synthetic macromolecules" is understood to mean modified chemical and/or natural molecules with a high molecular weight, for example a weight of 1 to 1000 kDa, for example polystyrene sulfonate and polyethylene glycol.

According to the invention, the expression "biological macromolecules" is understood to mean any biological macromolecules with a high molecular weight, for example a weight of 5 to 1000 kDa. They may be, for example, assembling biological macromolecules, for example that are assembled by covalent bonding, natural molecules, nucleic acids such as DNA and RNA, polysaccharides such as dextran, cellulose, starch, and proteins such as actin, fibrinogen and fibrin.

According to the invention, the expression "objects of microscopic size" is understood to mean any substance and/or object known to a person skilled in the art, the size of which is from 1 to 1000 µm, preferably from 1 to 100 µm.

According to the invention, the expression "objects of nanoscopic size" is understood to mean any particle known to a person skilled in the art, the size of which is less than 1 µm and/or 1000 nm, for example from 50 nm to 950 nm, from 1 to 100 nm.

According to the invention, the film may be formed, for example by polymerization of monomers via covalent bonds, by multimerization of proteins via covalent bonds, for example disulfide bridges, peptide bonds, via non-covalent bonds, for example salt bridges, hydrogen bonds, van der Waals forces, by sedimentation of microorganisms, by multiplication of microorganisms on a surface, by the secretion of polymers by these microorganisms, for example nucleic acids, proteins and polysaccharides, by polymerization of proteins, for example of plasma proteins or cell proteins.

The film may also be formed by the polymerization of monomers, for example of acrylamide, bisacrylamide, ethylene, propylene, vinyl and amino acids; by the deposition of an emulsion on a surface, for example a paint or a varnish, by the formation of hydrogels or aerogels, for example an agarose gel, agar gel or gelatin gel, for example an aerogel of silica, alumina, chromium (III) oxide or tin oxide or of SEAgel™.

According to the invention, the film may also be formed by evaporation/freeze drying of solutions, for example a solution of proteins, of DNA, of fat diluted in a solvent, for example of emulsions, for example a paint, a varnish, by liquid-solid phase change induced, for example, by a change of temperature, for example with melted butter, a moisturizing cream or a fat.

According to the invention, the action applied may be, for example, a mechanical, hydrodynamic or physical action.

According to the invention, the application may be carried out, for example, from 1 to 24 hours, from 1 to 60 minutes, from 1 to 5 minutes or from 1 to 60 seconds.

According to the invention, the expression "mechanical actions" is for example understood to mean the application of a brush, a spatula or a disk subjected to reciprocating movement along a surface, to a rotating or circular movement or to a pressure.

According to the invention, the expression "hydrodynamic actions" is for example understood to mean the rotating, for example using an agitator, for example at a rotational speed of 0.1 to 1000 rpm, of 5 to 300 rpm, and/or the application of a jet of liquid or gas, for example with a pump, and a jet of liquid or gas may be, for example, at a pressure of 1.01 to 10 bar, preferably from 1.1 to 2 bar.

According to the invention, the expression "physical actions" is for example understood to mean an irradiation, for example by electromagnetic radiation, for example the application of a light beam having a wavelength of 10 µm to 10 µm, from 100 nm to 1 µm. The beam may have an intensity, for example, of 0.01 W to 100 W, from 0.1 W to 10 W. It may also be, for example, a particle bombardment, for example with nuclear particles, for example neutrons, electrons, accelerated particles resulting from a particle accelerator, or from a radioactive source, for example grains of material, for example of sand, for example having a diameter of 50 to 500 µm, of salt, for example having a diameter of 50 to 500 µm, of metal, for example of copper, iron, zinc or aluminum, for example having a diameter of 10 to 500 µm.

Preferably, said at least one action applied in the process of the invention is a hydrodynamic action.

According to the invention, the process may comprise, independently, the application of at least two, or at least three actions described previously. For example, the process of the invention may comprise the application of a hydrodynamic action and of an electromagnetic action, for example an irradiation using ultraviolet rays followed, for example, by a rotation, or an irradiation with beta particles followed, for example, by the application of a jet of water.

The solution capable of being used in the present invention may be, for example, a liquid solution or a gas. The solution may be any solution known to a person skilled in the art. It may be, for example, a culture medium, for example a culture medium of eukaryotic and/or prokaryotic cells, a buffer medium, for example any buffer medium known to a person skilled in the art, for example a commercially available buffer medium, for example phosphate buffered saline (PBS), a biological sample, for example a sample of blood, of plasma, of urine or of cerebrospinal fluid, a saline solution, for example a physiological solution, a culture medium, for example the commercially available brain-heart infusion, a solvent, for example acetone, dimethylsulfoxide, ethanol, methanol, propanol, acetonitrile, ethyl acetate, ether, phenol, chloroform, tetrahydrofuran, or difluoroethylene, and/or a hydrocarbon, for example hexane, cyclohexane, benzene, octane, decane, petroleum, gasoline, and diesel fuel.

According to the invention, the gas may for example be air, oxygen, nitrogen, neon, argon, carbon dioxide, methane or ozone.

According to the invention, a liquid solution may have a density of 0.1 to 4 kg/l, of 0.3 to 3 kg/l; a gaseous solution may have a density of $10^{-15}$ kg/m$^3$ to 1000 kg/m$^3$, of $10^{-10}$ to 30 kg/m$^3$, of $10^{-5}$ to 3 kg/m$^3$.

Those skilled in the art, due to their general knowledge, will easily know how to determine the density of a solution. For example, the measurement of the density of the solution may be carried out, for example, by measuring the ratio of the mass to the volume, for example by weighing a solution of known volume.

According to the invention, the solution may be pretreated, for example, the solution may be purified, diluted or concentrated.

According to the invention, the solution may be purified by any process known to a person skilled in the art, for example by dialysis, by filtration, by ultrafiltration, by clarification and by centrifugation. For example, the filtration process may comprise passing the solution through a screen with pores of 0.2 to 100 µm, the ultrafiltration process may comprise, for example, a centrifugation at a speed of 1 to 3000 revolutions per minute for a time of 0.1 to 30 minutes, the dialysis process may be, for example, a process comprising a step of depositing the solution on to a dialysis membrane, for example having a cutoff threshold of 500 Da, said membrane floating on distilled water contained in a container. The clarification process may be, for example, a process comprising the addition to the solution of 0.1% (weight/weight) of bovine serum albumin.

According to the invention, the purification of the solution may advantageously make it possible to remove from the solution any contaminant and/or molecules capable of impairing the determination of the effect, for example the purification may make it possible to remove, independently, bacteria, viruses, proteins, chemical molecules, salts, grains of material and aggregates of molecules. Of course, those skilled in the art, due to their general knowledge, will know how to adapt the purification process as a function of the solution.

According to the invention, the solution may also be diluted, for example by any process known to a person skilled in the art, for example by serial dilution. The dilution may be carried out with any diluents known to a person skilled in the art. It may be, for example, a buffer solution, for example phosphate buffered saline, a saline solution, for example physiological serum, ethanol, DMSO, acetone, hexane and/or any solvent, hydrocarbon or solution described previously.

The solution may be diluted, for example, by a factor of 2 to 20000, of 5 to 500 or of 5 to 50.

The dilution of the solution may advantageously make it possible to modify the concentration of the components present in the solution, for example to reduce the concentration thereof, for example the dilution may make it possible to reduce the protein concentration. The dilution may thus make it possible to reduce the concentration of possible interferent compounds and thus to advantageously improve the specificity and/or the sensitivity of the process of the invention.

According to the invention, the solution may also be concentrated, for example by any process known to a person skilled in the art, for example by ultracentrifugation, by ultrafiltration, by evaporation or by freeze drying.

According to the invention, the purification, dilution and/or concentration of said solution may advantageously make it possible to adjust the density of said solution.

The adjustment of the density of the solution advantageously makes it possible to improve the sensitivity of the process of the invention, in particular by increasing, by decreasing or by canceling out the effect of the gravity force which pushes the particles toward the surface.

According to the invention, the volume of the solution used in the process may be, for example, from 0.3 µl to 100 ml, from 3 µl to 10 ml, from 30 µl to 1 ml.

According to the invention, the incubation of the solution may be carried out, for example, at a temperature of from −10° C. to 90° C., from 0° C. to 40° C. or from 15° C. to 25° C.

According to the invention, the incubation time may be carried out, for example, from 1 to 72 hours, from 2 to 48 hours, from 1 to 24 hours or from 1 to 60 minutes.

According to the invention, the term "effect" is understood, for example, to mean the abrasion, tearing, for example complete or partial tearing, destructuring, destruction, pulling off, detachment, piercing, appearance of cracks, crevices, holes or pores, swelling, shrinkage and/or inhibition of the formation of the film.

According to the invention, the process of the invention may be carried out with a plurality of particles, for example with at least 2 particles, with for example from 2 to 10000000, from 1000 to 1000000, from 10000 to 1000000, from 100000 to 1000000 or from 10000 to 100000. The plurality of particles advantageously makes it possible to detect directly, without a complex display device and without dye, the interaction between said substances unlike the prior art processes that use a single particle and require, for the detection of the interaction, complex display devices or dyes.

According to the invention, said at least two particles may be chosen from the group comprising electrically charged particles, magnetic particles, particles coated with at least one magnetic layer, magnetizable particles, particles coated with a magnetizable layer, electric, electromagnetic or electrifiable particles, bearing an electric charge or a mixture of two or more of these particles. In fact, it may be any particle that makes it possible to implement the present invention.

Advantageously, said particles may be a particle of any shape suitable for the implementation of the present invention, for example in the form of a bead or disk, of asymmetric geometric shape, for example with a flat face, etc.

Any appropriate size of magnetic particle may be used. The size may be chosen, for example, as a function of the size of the container of the solution. For example, the size of the particles may be less than a tenth of the size of the container, preferably less than a hundredth, more preferably still less than a thousandth of the size of the container. For example, the particle may have a size of, for example, 10 nm to 100 µm, of 0.1 to 10 µm.

According to the invention, the particles may be illuminated, for example by means of a light source. The illumination advantageously makes it possible to increase the contrast between the particle, and the solution.

The invention advantageously makes it possible, by using a plurality of particles, to detect small deteriorations caused by the action applied to the film. The use of a single magnetic or magnetizable particle and/or bead does not make it possible to detect these deteriorations. Moreover, there is a not insignificant risk of detecting non-specific phenomena, for example a partial formation of the film.

According to the invention, the observation can be carried out by any means known to a person skilled in the art. This may be, for example, an optical device, for example a microscope, a camera, a document scanner, for example an Epson Perfection V750 scanner, or a visual observation.

According to the invention, the observation may make it possible to measure, for example, the intensity, the contrast, or variance of an image, for example via any means known to a person skilled in the art, for example imaging software, for example ImageJ software that makes it possible, for example to measure for example differences in contrasts and intensities, corresponding for example to the particles, in zones from one image to another and thus to determine the differences from one observation to another. It may be a question, for example, of comparing the images obtained before and after application of the mechanical, hydrodynamic or physical action, for example by carrying out a subtraction between images, for example by measuring the correlation coefficient between the images.

According to the invention, the use of particles that emit a signal, for example colored, fluorescent, phosphorescent, luminescent or radioactive particles, may for example allow an automated observation.

According to the invention, the effect may be determined by viewing the distribution of the particles. For example, a particle-free zone may be, for example, a tear in the film, the non-dispersion of the particles makes it possible to determine the resistance of the film to the action.

According to the invention, the regrouping may be carried out with any means known to a person skilled in the art. This may be for example, when the particles are for example magnetic or magnetizable, a magnet or an electric or electromagnetic field making it possible, for example, to regroup said particles at one spot.

According to the invention, the term "spot" is for example understood to mean the regrouping at one location of the plurality of particles thus forming on the submerged surface a spot, a disk, a ring, a bar, a uniform geometric shape, for example a square, a lozenge or a triangle, or a mark.

According to the invention, the term "mark" is for example understood to mean a dark zone formed by the plurality of particles on the submerged surface.

According to the invention, the observation in step (e) may be carried out on a surface Si which may represent the observation surface, for example on a first image, for example on a surface of 1 to 10 000, from 10 to 900, from 50 to 700 or 100 to 500 pixels.

According to the present invention, the size of a pixel is defined by its width×height, for example the height of 0.018 to 0.660 mm, the width of 0.018 to 0.660 mm.

According to the invention, the observation in step (g) may be carried out on a surface $S_2$ which may represent the observation surface, for example on a second image, for example a surface equal to Si, a surface of 1.1 to 2.5 times that of Si, or of 0.5 to 0.9 times that of Si.

Advantageously, the aforementioned comparison may make it possible to measure the degree of the effect of the action, for example it may make it possible to measure the percentage and the amount of the film modified by the action.

According to the invention, the comparison of the observations may advantageously make it possible to determine the percentage of dispersion of the particles on the submerged surface and thus a value of the effect of the action on the film.

Moreover, the process of the invention makes it possible to obtain a reliable result, with a better sensitivity than the prior art processes.

Moreover, the process of the invention makes it possible to determine, without a chemical or biological reagent, the impact of the action on the film and, in addition, to quantify this impact in a reproducible and reliable manner in a short time and it is not dependent on a particular operator and/or device.

According to the invention, the field may be applied from the start and/or in the middle of the formation of the film.

According to the invention, the magnetic or electric or electromagnetic field may be any field that makes it possible to move said at least two particles on said submerged surface in said solution, for example an electromagnetic field or a magnetic field. The magnetic or electric or electromagnetic field may be generated, for example, by a magnet or by a solenoid. The magnet may for example be in the form of a bar, spike or part, etc. or any shape suitable for the implementation of the present invention. The field may for example be applied by any means known to the person skilled in the art, for example by pulsing, by gradual increase of the electromagnetic field, by variations of the electromagnetic field or by a combination of these applications.

According to the invention, the particles may be deposited on the surface in the form of a drop containing a binding substance that is soluble in the solution or which may break up during the application of an action.

According to the invention, the process also advantageously makes it possible to quantify the appearance of the marks and/or spots observed after application of the action.

The process of the invention may comprise, after step (f), a step (i) of quantifying (Q) the appearance of the marks and/or spots by measuring the mean standard deviation $D_1$. The determination of the mean standard deviation may be carried out by any process known to a person skilled in the art. The measurement may be carried out for example with the ImageJ software (Image Processing and Analysis in Java, http://rsb.info.nih.gov.ij), for example by measurement on an image observed in step (g) contained, for example, in an ellipse centered about the spot and/or the mark obtained in step (c), by calculation, by the approximate value of the variance of the shape of the spot or of the mark observed in step (g) equal to:

$$Q=(D*D-D_0*D_0)/(I*I),$$

where I is the measurement of the contrast, of the intensity of the marks as defined previously and $D_0$ is the mean standard deviation measured with the ImageJ software of the background of the well around the mark, for example in an ellipse situated in contact with the mark but not including the mark itself.

Advantageously, the present invention makes it possible to determine the formation and destruction of biofilms of microorganisms, of films formed, for example by paints, by foodstuffs, by samples of natural or industrial media, by biological samples, for example biofilms of microorganisms which may be films consisting of one or more species of microorganisms (bacteria, fungi, algae or protozoa), adhering together and to a surface, and secreting no, little or a variable amount of an adhesive and protective matrix generally consisting of polysaccharides.

Moreover, the process of the invention makes it possible to obtain a reliable result with a better sensitivity and a better specificity than the prior art processes.

Furthermore, the process of the invention makes it possible to obtain a reproducible result and therefore enables an effective and useful comparison of the measurements carried out with the process of the invention.

Other advantages will again become apparent to a person skilled in the art on reading the examples below, illustrated by the appended figures, given by way of illustration.

BRIEF DESCRIPTION OF THE FIGURES

FIG. 2A represents the photograph of 4 strips indicated sw 1 to sw 4 respectively comprising the following bacteria: *Listeria monocytogenes, Escherichia coli* DH5 α, *Staphylococcus xylosus, Staphylococcus carnosus* and magnetic particles before hydrodynamic action.

FIG. 2B represents the photograph of 4 strips indicated sw 1 to sw 4 respectively comprising the following bacteria: *Listeria monocytogenes, Escherichia coli* DH5 α, *Staphylococcus xylosus, Staphylococcus carnosus* and magnetic particles after hydrodynamic action.

EXAMPLES

Example 1

Measurement of the Effect of a Hydrodynamic Action on Films of Proteins

In this example, the method is applied to the study of the resistance of films formed from solutions that are rich in proteins.

2.4 ml of solutions, respectively, of water, of BHI (BD-DIFCO, France) at 37 g/l, of peptone (Fluka) at 5 g/l and of Bacto (trademark) tryptone (BD-DIFCO, France) at 5 g/l were prepared. These solutions were supplemented with a solution of paramagnetic microbeads (Ton006N, Biofilm Control, France) in a proportion of 10 µl/ml. These solutions were then deposited in a proportion of 100 µl per well, in the wells, respectively, A and E, B and F, C and G, D and H, of 2 strips of flat-bottom wells (reference: MSW002B, BioFilm Control, France). The strips were placed on magnetized test blocks (BKT-MSW002 BioFilm Control, France), and the whole assembly was placed in a thermostatic oven (reference BC240, Firelabo, France) stabilized at 37° C. for 2 h 30 min.

The strips were then placed on an orbital shaker (Variomag Monoshake, H+P Labortechnik, Germany) adjusted to 30%+/−10% of its maximum rotational speed, in order to subject them to a hydrodynamic action successively for 0 s, 5 s, 5 s, 10 s, 10 s, 10 s, 10 s, 20 s, 20 s, 20 s, 30 s, 30 s, 30 s, 30 s, thus adding up to total shaking times of 0 s, 5 s, 10 s, 20 s, 30 s, 40 s, 50 s, 60 s, 80 s, 100 s, 120 s, 150 s, 180 s, 210 s and 240 s.

After each shaking action, the strips were placed on a document scanner (Perfection V-750 PRO, Epson, USA) with which image acquisition was carried out with the EpsonScan software (Epson, USA).

Figure 1A:
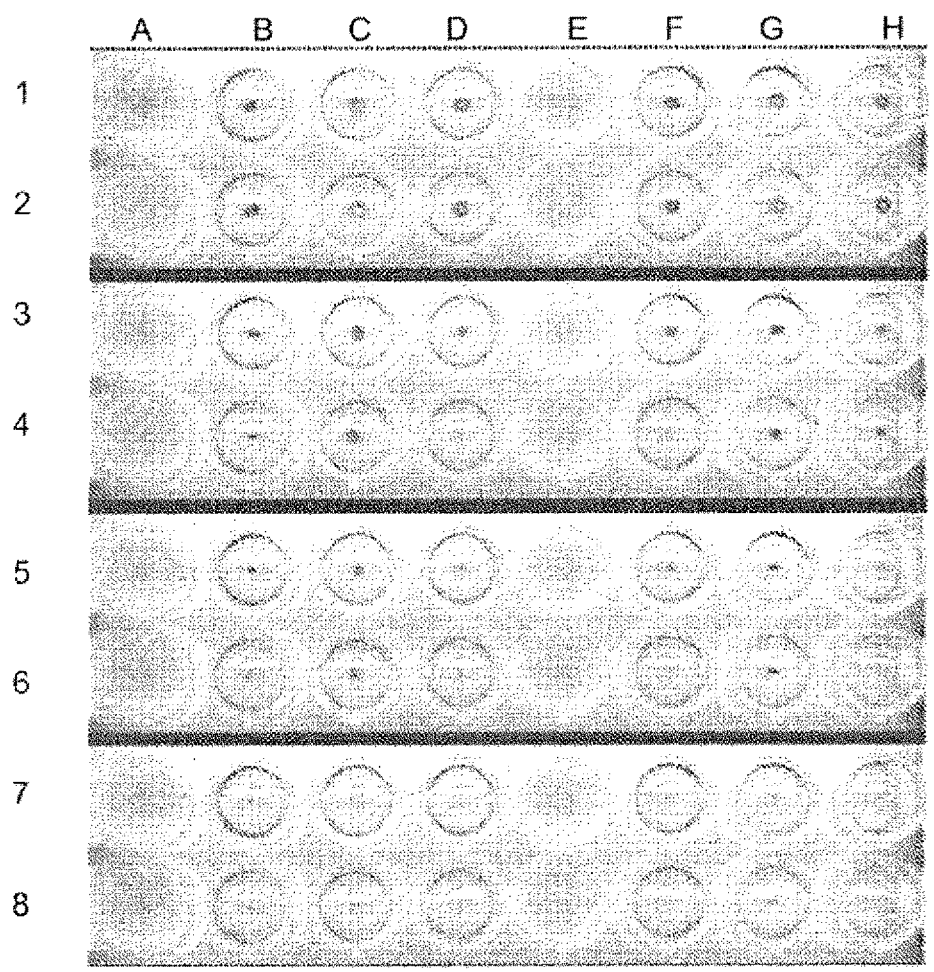
FIG. 1A represents a photograph of 6 strips indicated from 1 to 6 respectively comprising in the wells of columns A and E, water and paramagnetic microbeads, of columns B and F, BHI at 37 g/l and paramagnetic microbeads, of columns C and G, peptone at 5 g/l and paramagnetic microbeads, of columns D and H, tryptone at 5 g/l and paramagnetic microbeads. The lines correspond to the observation of the wells after an incubation of 2 h 30 min at 37° C., respectively the lines 1 and 2 before shaking, the lines 3 and 4 after 20 seconds of shaking, the lines 5 and 6 after 60 seconds of shaking and the lines 7 and 8 after 240 seconds of shaking.
Figure 1:
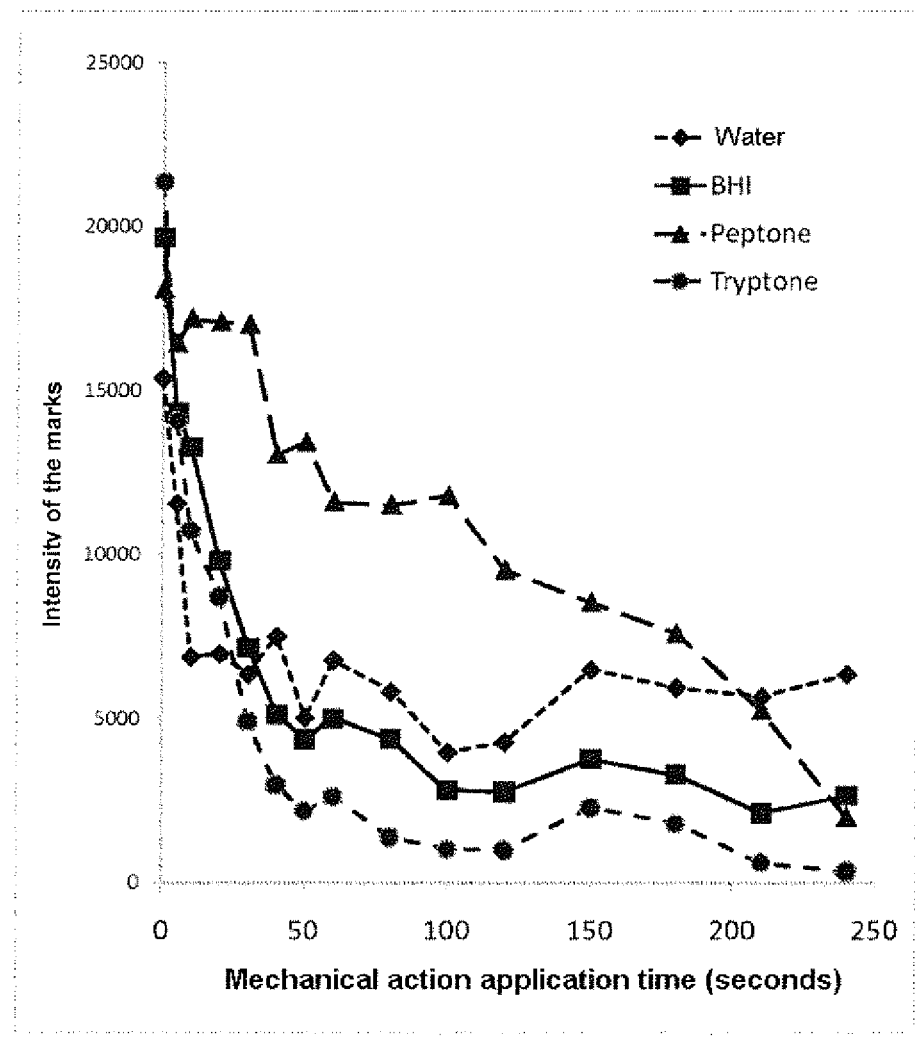
FIG. 1B represents a diagram of the variation of the attributable intensity (Iatt) of the marks (on the x-axis) as a function of the hydrodynamic action time (T) in seconds (y-axis). The solid squares represent the values obtained for the wells comprising the brain-heart infusion (BHI) medium, the solid triangles represent the values obtained for the wells comprising peptone, the solid circles represent the values obtained for the wells comprising tryptone and the solid lozenges represent the values obtained for the wells comprising water.

The images reproduced in FIG. 1A for shaking times of 0 s, 20 s, 60 s and 240 s were obtained by adding the red, green and blue components of the color images obtained with the scanner using the ImageJ software (http://rsb.info.nih.gov.ij) and cutting out images obtained with different adjustments of the contrast. Clearly defined spots are visible in all the wells.

The spots and marks were quantified by carrying out two measurements, respectively $I_1$ and $I_2$, of the mean intensity of the image contained in an ellipse centered about the surface spot or mark, respectively, $Si=100$ to 500 pixels and $S_2=1.1 \times Si$ to $2.5 \times Si$, with the ImageJ software.

An approximate measurement of the intensity ($I_{att}$) attributable to the dark spot or mark observed in the images is obtained by carrying out the following calculation:

$$I_{att} = Si \times (I_2 \times Si - I_1 \times Si)/(S_2 - S_1) - I_1 \times Si$$

The mean values of the intensities thus obtained are reproduced in FIG. 1B and in table 1 below.

TABLE 1

Measurement results of the intensity measured

| Hydrodynamic action application time in seconds | Intensity of the marks | | | |
|---|---|---|---|---|
| | Water | BHI | Peptone | Tryptone |
| 0 | 15356 | 19650 | 18068 | 21335 |
| 5 | 11538 | 14306 | 16421 | 14074 |
| 10 | 6878 | 13273 | 17179 | 10715 |
| 20 | 6975 | 9803 | 17081 | 8701 |
| 30 | 6361 | 7180 | 16995 | 4907 |
| 40 | 7494 | 5137 | 13027 | 2978 |
| 50 | 5031 | 4368 | 13421 | 2176 |
| 60 | 6772 | 5012 | 11587 | 2627 |
| 80 | 5823 | 4391 | 11498 | 1378 |
| 100 | 3983 | 2825 | 11777 | 1017 |
| 120 | 4287 | 2771 | 9509 | 993 |
| 150 | 6495 | 3777 | 8523 | 2285 |
| 180 | 5942 | 3304 | 7575 | 1799 |
| 210 | 5668 | 2114 | 5242 | 607 |
| 240 | 6338 | 2644 | 1993 | 337 |

As represented in FIG. 1B and in the table above, the image intensity varies as a function of the shaking time and makes it possible to measure, for example, the resistance of films. As demonstrated in this example, the process of the invention makes it possible to determine the effect of an action, for example a hydrodynamic action, on a film. In particular, the process of the invention makes it possible to determine the resistance of films relative to one another.

Example 2

Measurement of the Effect of a Hydrodynamic Action on Biofilms of Various Species In this example, the process of the invention makes it possible to study the resistance of biofilms formed by various bacterial species.

Cultures of 16 hours in brain-heart infusion medium (BHI, BD-DIFCO (France)) of the following 4 microorganisms: *Listeria monocytogenes*, *Escherichia coli* DH5 α, *Staphylococcus xyloses*, *Staphylococcus carnosus* were adjusted to an optical density, at a wavelength of 600 nm, $DO_{600\ nm}=0.004$ by dilution with sterile BHI, supplemented with a solution of paramagnetic microbeads (Ton005N, BioFilm Control, France) at a concentration of 10 µl/ml. The measurement of the optical density was carried out with a spectrophotometer (Biomate, Thermo Scientific, France). The adjusted culture comprising the paramagnetic microbeads was deposited in flat-bottom wells (reference: MSW002B, BioFilm Control, France) in a proportion of 200 µl/well in the wells referenced F, G and H of 4 strips, respectively referenced sw1, sw2, sw3 and sw4. 200 µl of sterile BHT supplemented with a solution of paramagnetic microbeads (Ton005N, BioFilm Control, France) in a proportion of 10 µl/ml were deposited in the wells E of each of the strips.

The distribution of the various depositions is represented in table 2 below.

TABLE 2

|  | E | F | G | H |
|---|---|---|---|---|
| Sw1 | Sterile BHI | *Listeria monocytogenes* | *Listeria monocytogenes* | *Listeria monocytogenes* |
| Sw2 | Sterile BHI | *Escherichia coli* DH5 α | *Escherichia coli* DH5 α | *Escherichia coli* DH5 α |
| Sw3 | Sterile BHI | *Staphylococcus xylosus* | *Staphylococcus xylosus* | *Staphylococcus xylosus* |
| Sw4 | Sterile BHI | *Staphylococcus carnosus* | *Staphylococcus carnosus* | *Staphylococcus carnosus* |

Each strip was placed independently on a magnetized test block (BKT-MSW002 BioFilm Control, France) placed in covered rectangular boxes of 18×12×7 cm containing two 25 ml beakers containing 20 ml of water. The assembly was then placed in a thermostatic oven (reference BC240, Firelabo, France) stabilized at 30° C. for the strips sw1 and sw2 and stabilized at 37° C. for the strips sw3 and sw4 for 8 hours.

Figure 2A:
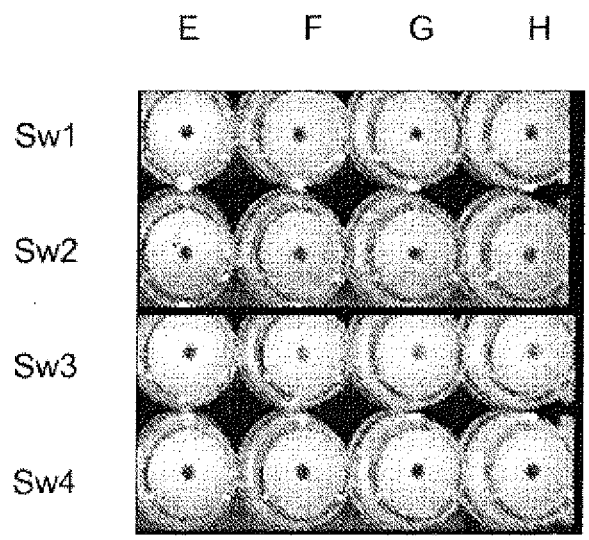
FIGS. 2A and 2B are photographs of well strips.
Figure 2:
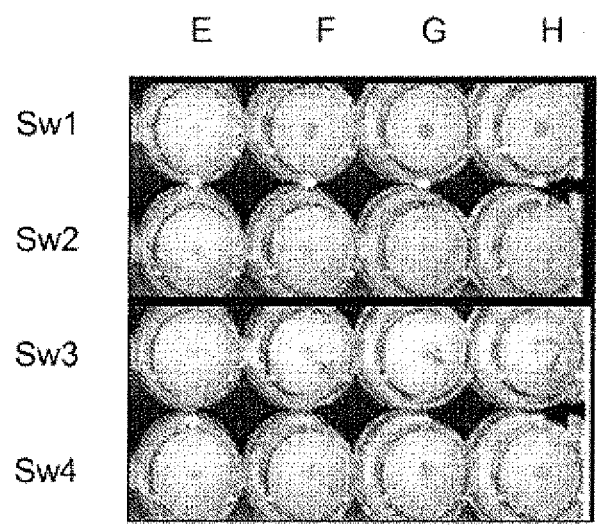

The strips were then placed independently on a document scanner (Perfection V-750 PRO, Epson, USA) with which an image acquisition was carried out with the Epson Scan software (Epson, USA). The final images reproduced in FIG. 2A were obtained by adding the red, green and blue components of the color images obtained with the scanner using the ImageJ software (Image Processing and Analysis in Java, http://rsb.info.nih.gov.ij) and cutting out the images obtained with various adjustments of the contrast. Clearly defined spots are visible in all the wells.

The strips were then placed on an orbital shaker (Variomag Monoshake, H+P Labortechnik, Germany) adjusted to 60%+/−20% of its maximum rotational speed for 10 seconds. This step corresponds to subjecting the film formed in the culture to a hydrodynamic action.

A second image acquisition was carried out under the same conditions as the first image. The image thus obtained corresponds to FIG. 2B. In this figure, spots and marks that are more or less clearly defined are visible, and their appearance depends on the bacterial strain that formed the biofilm. The spots in line E are notably less intense, which corresponds to a maximum dispersion of the paramagnetic microbeads under the hydrodynamic action.

The spots and marks were quantified by carrying out two measurements, respectively $I_1$ and $I_2$, of the mean intensity of the image contained in an ellipse centered about the surface spot or mark, respectively, $S_1=100$ to 500 pixels and $S_2=1.1 \times S_1$ to $2.5 \times S_1$, with the ImageJ software.

An approximate measurement of the intensity ($I_{att}$) attributable to the dark spot or mark observed in the images is obtained by carrying out the following calculation:

$$I_{att}=Si \times (I_2 \times S_2 - I_1 \times Si)/(S_2 - Si) - I_1 \times Si$$

Figure 3A:
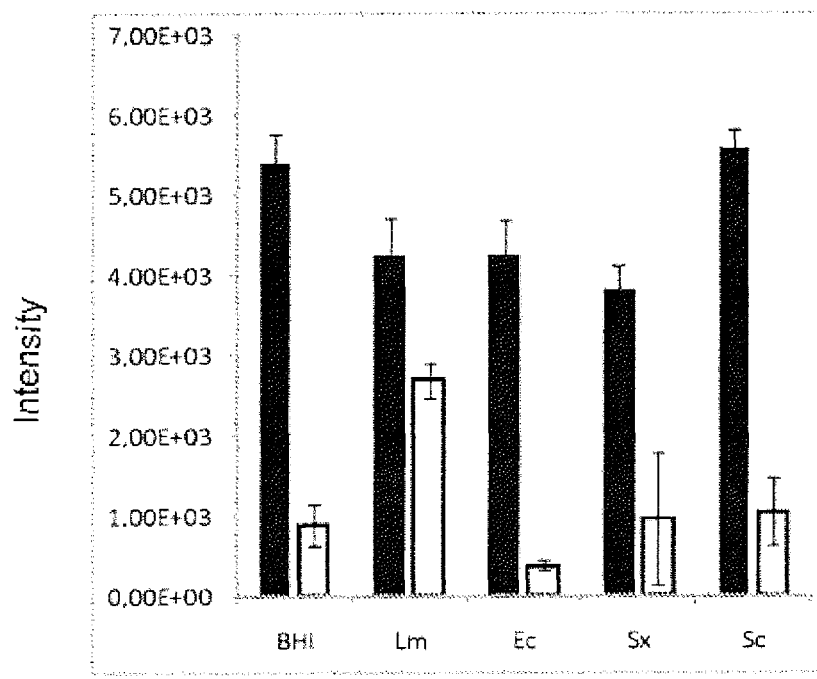
FIG. 3A is a bar chart representing the results of the intensity (I) (y-axis) as a function of the bacterium (x-axis), BHI represents the wells without bacteria, Lm: *Listeria monocytogenes*, Ec: *Escherichia coli*. DH5α, Sx: *Straphylococcus xylosus*, Se: *Straphylococcus carnosus*. Black bars: values before shaking, white bars: values after shaking.
Figure 3:
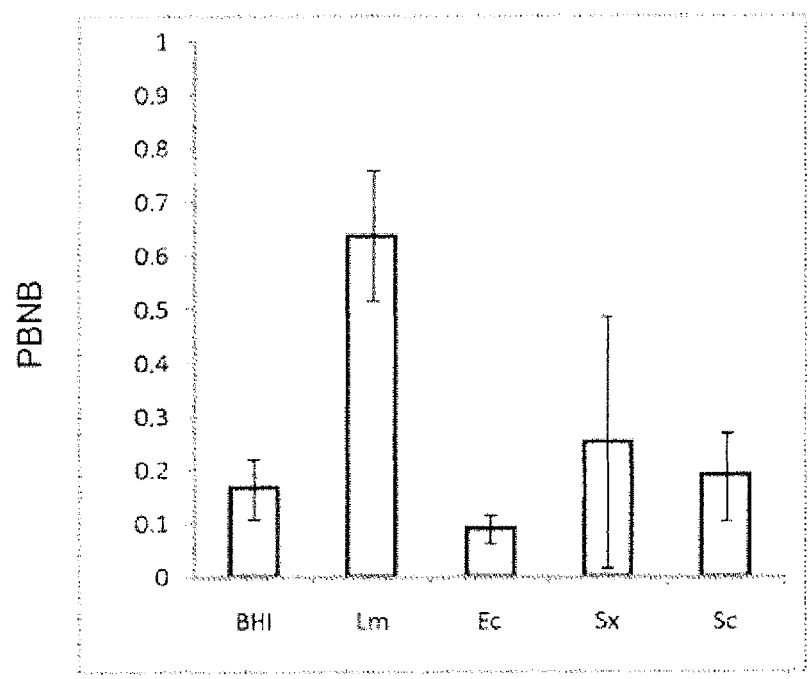
FIG. 3B is a bar chart representing a standardization of the values obtained in 3A, corresponding to the proportion of biofilm not broken up (PBNB) after the hydrodynamic action (y-axis) as a function of the bacterium (x-axis). BHI represents the wells without bacteria, Lm: *Listeria monocytogenes*, Ec: *Escherichia coli* DH5α, Sx: *Staphylococcus xylosus*, Se: *Staphylococcus carnosus*.
FIG. 3C is a bar chart representing the quantification Q (y-axis) as a function of the bacteria. BHI represents the wells without bacteria, Lm: *Listeria monocytogenes*, Ec: *Escherichia coli* DH5α, Sx: *Staphylococcus xylosus*, Se: *Staphylococcus carnosus*.
Figure 3:
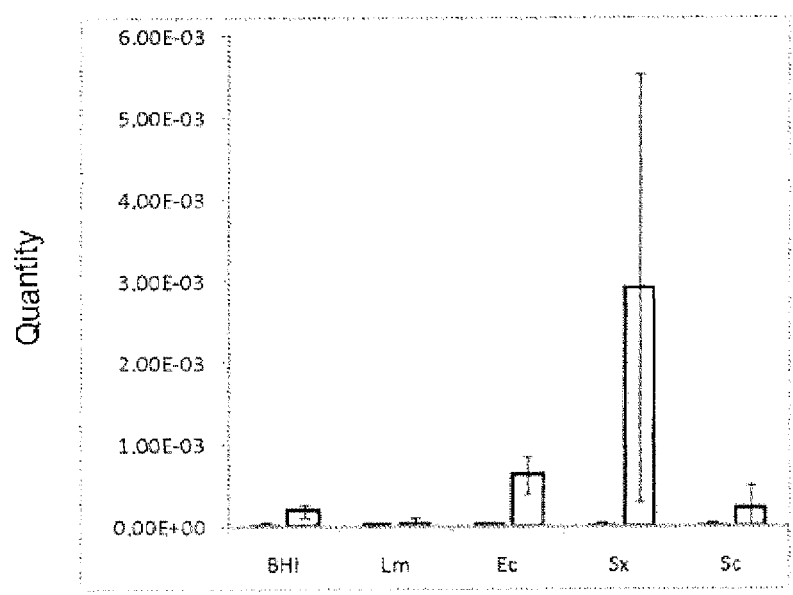

The mean values of the intensities thus obtained are reproduced in FIG. 3A and in table 3 below, the error bars corresponding to the standard deviation of the measurements made.

TABLE 3

Measurements results of the intensity measured

|  | Before magnetization | | After magnetization | |
|---|---|---|---|---|
| $I_{att}$ | Mean | Standard deviation | Mean | Standard deviation |
| BHI | 5.40E+03 | 3.45E+02 | 8.86E+02 | 2.49E+02 |
| Lm | 4.24E+03 | 4.72E+02 | 2.69E+03 | 2.16E+02 |
| Ec | 4.24E+03 | 4.50E+02 | 3.80E+02 | 7.41E+01 |
| Sx | 3.82E+03 | 3.03E+02 | 9.49E+02 | 8.20E+02 |
| Sc | 5.57E+03 | 2.30E+02 | 1.04E+03 | 4.23E+02 |

The raw intensities after magnetization are standardized by dividing them by the raw intensity before magnetization and make it possible to obtain an approximate measurement of the proportion of biofilm not broken up by the hydrodynamic action (PBNB). The results obtained for this example are reproduced in FIG. 3B and in table 4 below, the error bars corresponding to the standard deviation of the measurements.

TABLE 4

| Medium | Mean | Standard deviation |
|---|---|---|
| BHI | 0.16393578 | 0.05648906 |
| Lm | 0.63556509 | 0.12167536 |
| Ec | 0.08963821 | 0.0269836 |
| Sx | 0.24868618 | 0.2345908 |
| Sc | 0.1874682 | 0.08374593 |

The appearance of the spots and marks may also be quantified (Q value) by deducing it from the mean standard deviation D1 measured with the ImageJ software of the image contained in an ellipse centered about the spot or mark by the calculation of the approximate value of the variance of the shape of the spot or mark equal to:

$$Q=(D1*D1-D0*D0)/(I*I),$$

where I is the intensity calculated as described above and D0 is the mean standard deviation measured with the ImageJ software of the background of the spot around the mark.

The results obtained for this example are reproduced in FIG. 3C and in table 5 below, the error bars corresponding to the standard deviation of the measurements.

TABLE 5

|  | Before magnetization | | After magnetization | |
|---|---|---|---|---|
| Standardized variances | Mean deviation | Standard | Mean deviation | Standard |
| BHI | 1.88E−04 | 7.63E−05 | 3.38E−05 | 8.57E−06 |
| Lm | 1.98E−05 | 9.43E−05 | 3.54E−05 | 1.11E−05 |
| Ec | 6.33E−04 | 2.29E−04 | 3.97E−05 | 7.11E−06 |
| Sx | 2.91E−03 | 2.61E−03 | 2.80E−05 | 9.39E−06 |
| Sc | 2.17E−04 | 2.98E−04 | 2.84E−05 | 8.56E−06 |

As demonstrated in this example, the process of the invention makes it possible to determine the effect of an action, for example a hydrodynamic action, on a biofilm. In particular, the process of the invention makes it possible to determine the resistance of films relative to one another.

Moreover, the process of the invention makes it possible to detect, very sensitively and rapidly, the deviation of the particles and the effect of the action on the film.

Example 3

Measurement of the Effect of a Hydrodynamic Action on Biofilms in the Process of being Formed In this example, the devices and products used are identical to those from the preceding example.

A culture of 16 hours in BHI medium (BD-DIFCO (France)) of *Listeria monocytogenes* is adjusted to $DO_{600\ nm}$=0.004 by dilution with sterile BHI, supplemented with a solution of paramagnetic microbeads (Ton005N, BioFilm Control, France) in a proportion of 10 µl/ml, then 200 µl/well were deposited in the flat-bottom wells (reference: MSW002B, BioFilm Control, France) indicated F, G and H of 6 strips, respectively sw0, sw2, sw4, sw6, sw8 and sw24. 200 µl of sterile BHI supplemented with 10 µl/ml of a solution of paramagnetic microbeads (Ton005N, BioFilm Control, France) were deposited in the wells E of each of the strips.

The distribution of the various depositions is represented in table 6 below.

TABLE 6

| | E | F | G | G |
|---|---|---|---|---|
| Sw0 | Sterile BHI | *Listeria monocytogenes* | *Listeria monocytogenes* | *Listeria monocytogenes* |
| Sw2 | Sterile BHI | *Listeria monocytogenes* | *Listeria monocytogenes* | *Listeria monocytogenes* |
| Sw4 | Sterile BHI | *Listeria monocytogenes* | *Listeria monocytogenes* | *Listeria monocytogenes* |
| Sw8 | Sterile BHI | *Listeria monocytogenes* | *Listeria monocytogenes* | *Listeria monocytogenes* |
| Sw24 | Sterile BHI | *Listeria monocytogenes* | *Listeria monocytogenes* | *Listeria monocytogenes* |

The strips were placed on magnetized test blocks (BKT-MSW002 BioFilm Control, France) placed in covered rectangular boxes of 18×12×7 cm containing two 25 ml beakers containing 20 ml of water, the whole assembly being placed in a thermostatic oven (reference BC240, Firelabo, France) stabilized at 30° C. for, respectively, 0 h, 2 h, 4 h, 6 h, 8 h and 24 h.

Figure 4:
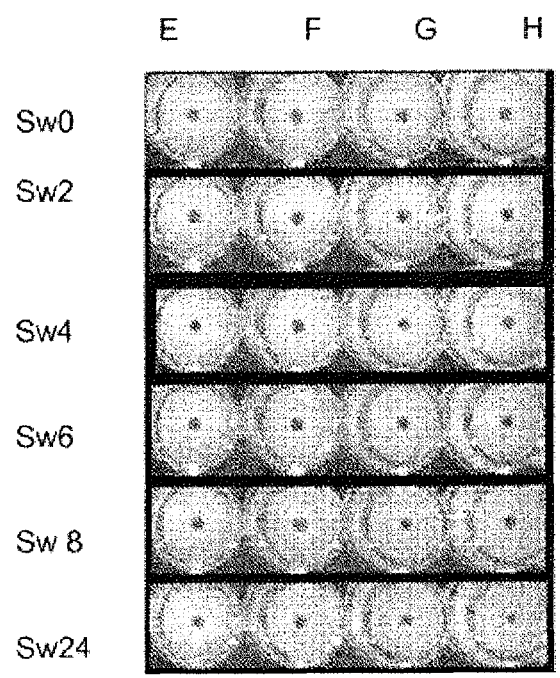
FIG. 4A represents a photograph of 6 strips indicated sw 0, sw 2, sw 4, sw 6, sw 8 and sw 24 (respectively after 0, 2, 4, 6, 8 and 24 hours of culturing at 37° C.) comprising, in the well E BHI medium and magnetic particles, in the wells F, G and H the bacteria *Listeria monocytogenes* in BHI medium with magnetic particles before hydrodynamic action.
FIG. 4B represents a photograph of 6 strips indicated sw 0, sw 2, sw 4, sw 6, sw 8 and sw 24 (respectively after 0, 2, 4, 6, 8 and 24 hours of culturing at 37° C.) comprising, in the well E BHI medium and magnetic particles, in the wells F, G and H the bacteria *Listeria monocytogenes* in BHI medium with magnetic particles after hydrodynamic action.
Figure 4:
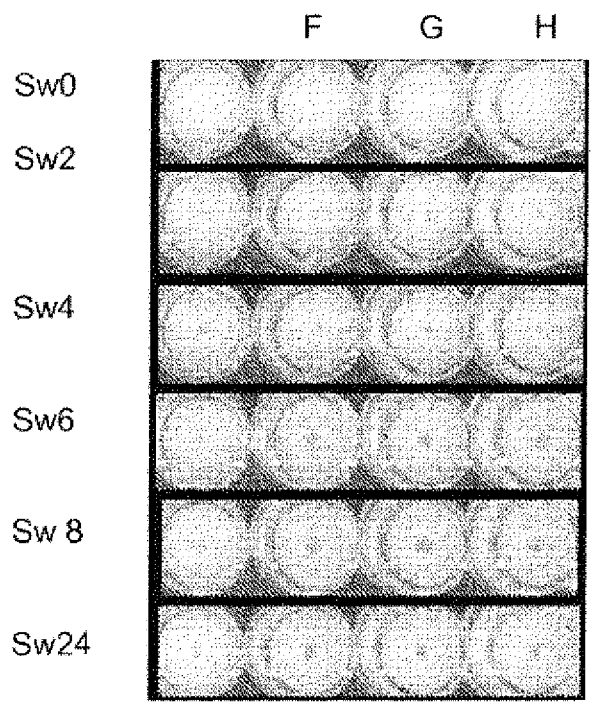

The strips were then placed on a document scanner (Perfection V-750 PRO, Epson, USA) with which an image acquisition was carried out with the EpsonScan software (Epson, USA). The final images reproduced in FIG. 4A were obtained by adding the red, green and blue components of the images of the red component of the color images obtained with the scanner using the ImageJ software (http://rsb.info.nih.gov.ij) and cutting out the images obtained with various adjustments of the contrast. The image obtained is represented in FIG. 4A. Clearly defined spots are visible in all the wells.

The strips were then placed on an orbital shaker (Variomag Monoshake, H+P Labortechnik, Germany) adjusted to 60%+/−20% of its maximum rotational speed for 10 seconds in order to subject them to a hydrodynamic action.

A second image acquisition was carried out under the same conditions as the first image and the final image is reproduced in FIG. 4B. The spots and marks that are more or less clearly defined are visible, and their appearance depends on the bacterial strain that formed the biofilm.

The spots and marks were quantified by carrying out two measurements, with the ImageJ software, respectively $I_1$ and $I_2$, of the mean intensity of the image contained in an ellipse centered about the surface spot or mark, respectively, $S_1$=100 to 500 pixels and $S_2$=1.1×$S_1$ to 2.5×$S_1$ An approximate measurement of the intensity ($I_{att}$) attributable to the dark spot or mark observed in the images is obtained by carrying out the following calculation:

$$I_{att}=Si\times(I_2\times S_2-I_1\times Si)/(S_2-Si)-h\times S_1$$

Figure 5:
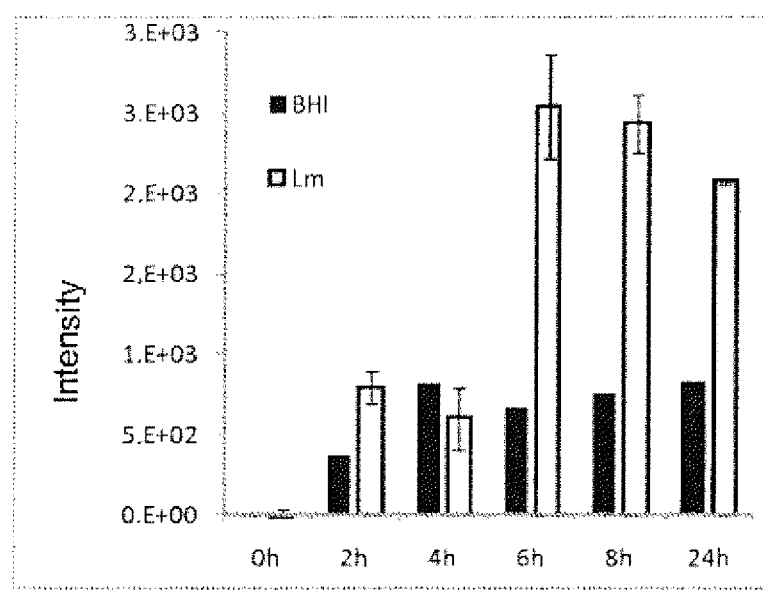
FIG. 5A is a bar chart representing the results of the intensity (I) (y-axis) as a function of the time (x-axis) at 0, 2, 4, 6, 8 or 24 hours. The empty bars correspond to the results obtained with *Listeria monocytogenes* (Lm), the black bars to the results without bacteria (BHI).
FIG. 5B is a bar chart representing the proportion of biofilm not broken up (PBNB) after the hydrodynamic action (y-axis) as a function of the time (x-axis) at 0, 2, 4, 6, 8 or 24 hours. The empty bars correspond to the results obtained with *Listeria monocytogenes* (Lm), the black bars to the results without bacteria (BHI).
FIG. 5C is a bar chart representing the quantification Q (y-axis) as a function of the time (x-axis) at 0, 2, 4, 6, 8 or 24 hours. The empty bars correspond to the results obtained with *Listeria monocytogenes* (Lm), the black bars to the results without bacteria (BHI).
Figure 5:
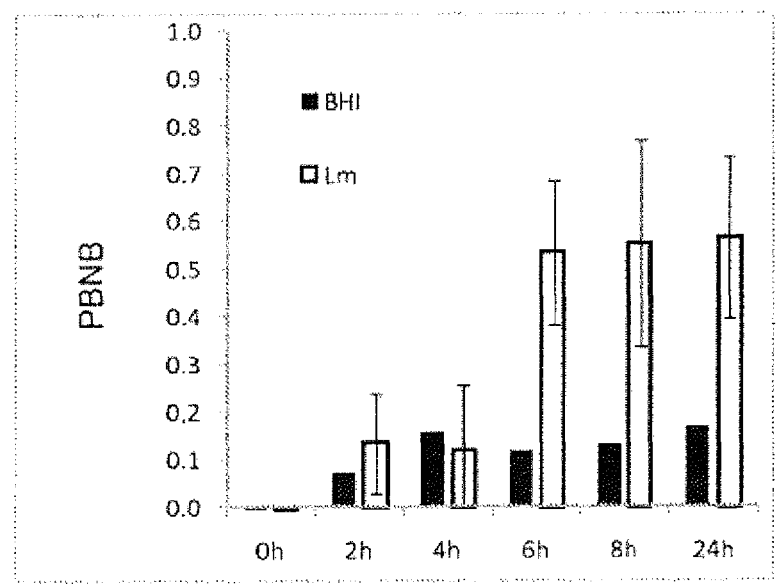

The mean values of the intensities thus obtained are reproduced in FIG. 5A and in table 7 below, the error bars corresponding to the standard deviation of the measurements made.

TABLE 7

| Time | BHI | Lm | Standard deviation Lm |
|---|---|---|---|
| 0 h | −1.72E+01 | −5.82E+00 | 3.55E+01 |
| 2 h | 3.74E+02 | 7.94E+02 | 9.81E+01 |
| 4 h | 8.14E+02 | 6.02E+02 | 1.95E+02 |
| 6 h | 6.64E+02 | 2.54E+03 | 3.29E+02 |
| 8 h | 7.52E+02 | 2.44E+03 | 1.79E+02 |
| 24 h | 8.26E+02 | 2.07E+03 | 2.19E+01 |

The raw intensities after magnetization were standardized by dividing them by the raw intensity before magnetization and make it possible to obtain an approximate measurement of the proportion of biofilm not broken up (PBNB) by the hydrodynamic action. These results are reproduced in FIG. 5B and in table 8 below.

TABLE 8

| Time | BHI | Lm | Standard deviation Lm |
|---|---|---|---|
| 0 h | −0.00360422 | −0.0011256 | 1.04E−03 |
| 2 h | 0.06975705 | 0.13379324 | 1.05E−01 |
| 4 h | 0.15521974 | 0.11969938 | 1.34E−01 |
| 6 h | 0.11833857 | 0.533572 | 1.52E−01 |
| 8 h | 0.1325017 | 0.5516224 | 2.17E−01 |
| 24 h | 0.16997323 | 0.5647522 | 1.72E−01 |

The appearance of the spots and marks may also be quantified Q by deducing it from the mean standard deviation D1 measured with the ImageJ software of the image contained in an ellipse centered about the spot or mark by the calculation of the approximate value of the variance of the shape of the spot or mark according to the following formula:

$$Q=(D1*D1-D0*D0)/(I*I),$$

where I is the intensity calculated as described above and D0 is the mean standard deviation measured with the ImageJ software of the background of the spot around the mark or the spot.

Figure 5C:
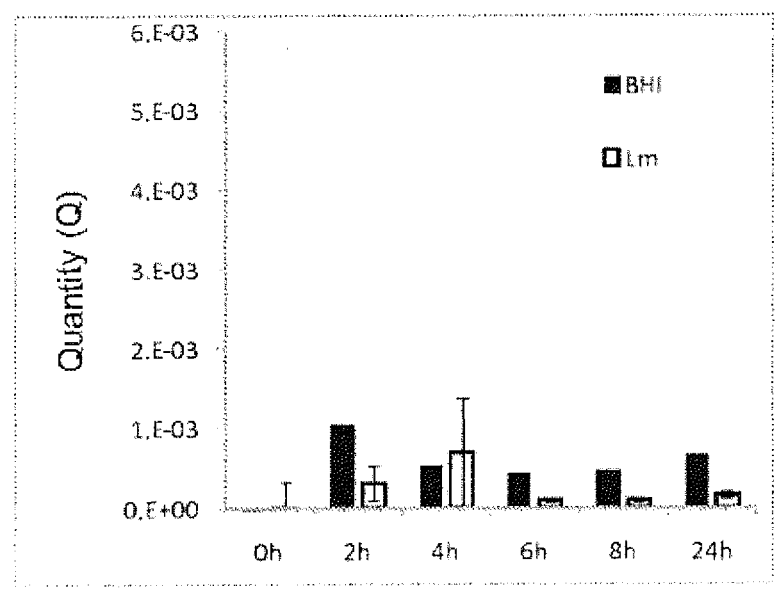

The results obtained for this example are reproduced in FIG. 5C, the error bars corresponding to the standard deviation of the measurements.

TABLE 9

| Time | BHI | Lm | Standard deviation Lm |
|---|---|---|---|
| 0 h | −4.25E−03 | −3.30E−03 | 0.003635176 |
| 2 h | 1.06E−03 | 3.20E−04 | 0.000216958 |
| 4 h | 5.36E−03 | 6.81E−04 | 0.000686718 |
| 6 h | 4.35E−04 | 9.43E−05 | 1.33109E−05 |
| 8 h | 4.63E−04 | 1.08E−04 | 3.16769E−05 |
| 24 h | 6.71E−04 | 1.64E−04 | 3.72707E−05 |

As demonstrated in this example, the process of the invention makes it possible to determine the effect of an action, for example a hydrodynamic action, on a biofilm. In particular, the process of the invention makes it possible to determine the resistance of films relative to one another.

Moreover, the process of the invention makes it possible to detect, very sensitively and rapidly, the deviation of the particles and the effect of the action on the film.

Example 4

Measurement of the Effect of an Antibiotic and of a Hydrodynamic Action on Biofilms In this example, the devices and products used are identical to those of the preceding example.

A culture of 16 hours in BHI medium (BD-DIFCO (France)) of *Staphylococcus aureus* CIP 76.25A is adjusted to $DO_{600\ nm}$=0.004 by dilution with sterile BHI, supplemented with 10 µl/ml of a solution of paramagnetic microbeads (Ton005N, BioFilm Control, France) and 200 µl/well were deposited in the flat-bottom wells, respectively lines 1 to 9, and respectively columns G to B, of a plate (reference: MMB002B BioFilm Control, France). Each solution was supplemented with antibiotics, respectively, ampicillin C=0.5 µg/ml, ceftazidime C=16 µg/ml, chloramphenicol C=16 µg/ml, erythromycin C=0.5 µg/ml, piperacillin C=1 µg/ml, tetracycline C=2 µg/ml, gentamicin C=16 µg/ml, ciprofloxacin C=2 µg/ml, trimethoprim C=64 µg/ml, at various concentrations, respectively, 0×C, 4×C, 2×C, C, 0.5×C and 0.25×C.

Deposited in the wells of column H, respectively lines 1 to 9, were 200 µl of BHI supplemented with 10 µl/ml of a solution of paramagnetic microbeads (Ton005N, BioFilm Control, France) and with antibiotic at a concentration of 4×C of, respectively, ampicillin C=0.5 µg/ml, ceftazidime C=16 µg/ml, chloramphenicol C=16 µg/ml, erythromycin C=0.5 µg/ml, piperacillin C=1 µg/ml, tetracycline C=2 µg/ml, gentamicin C=16 µg/ml, ciprofloxacin C=2 µg/ml, trimethoprim C=64 µg/ml.

Column A corresponds to sterile PHI control wells supplemented only with a solution of paramagnetic microbeads.

Column G corresponds to *Staphylococcus aureus* CIP 76.25a viability controls. Column H corresponds to sterile BHI control wells supplemented with a solution of paramagnetic microbeads in the presence of a maximum dose of antibiotics.

The distribution of the various depositions is represented in table 10 below.

TABLE 10

| | H | G | F | E | D | C | B | A |
|---|---|---|---|---|---|---|---|---|
| *Staphylococcus aureus* | − | + | + | + | + | + | + | − |
| 1 Ampicillin | 4 × C | 0 × C | 4 × C | 2 × C | C | 0.5 × C | 0.25 × C | 0 × C |
| 2 Ceftazidime | 4 × C | 0 × C | 4 × C | 2 × C | C | 0.5 × C | 0.25 × C | 0 × C |
| 3 Chloramphenicol | 4 × C | 0 × C | 4 × C | 2 × C | C | 0.5 × C | 0.25 × C | 0 × C |
| 4 Erythromycin | 4 × C | 0 × C | 4 × C | 2 × C | C | 0.5 × C | 0.25 × C | 0 × C |
| 5 Piperacillin | 4 × C | 0 × C | 4 × C | 2 × C | C | 0.5 × C | 0.25 × C | 0 × C |
| 6 Tetracyclin | 4 × C | 0 × C | 4 × C | 2 × C | C | 0.5 × C | 0.25 × C | 0 × C |
| 7 Gentamicin | 4 × C | 0 × C | 4 × C | 2 × C | C | 0.5 × C | 0.25 × C | 0 × C |
| 8 Ciprofloxacin | 4 × C | 0 × C | 4 × C | 2 × C | C | 0.5 × C | 0.25 × C | 0 × C |
| 9 Trimethoprim | 4 × C | 0 × C | 4 × C | 2 × C | C | 0.5 × C | 0.25 × C | 0 × C |

The strips were placed on magnetized test blocks (BKT-MWS002 BioFilm Control, France) placed in covered rectangular boxes of 18×12×7 cm containing two 25 ml beakers containing 20 ml of water. The assembly was placed in a thermostatic oven (reference BC240, Firelabo, France) stabilized at 37° C. for 16 hours.

The strips were then placed on a document scanner (Perfection V-750 PRO, Epson, USA) with which an image acquisition was carried out with the EpsonScan software (Epson, USA).

Figure 6:
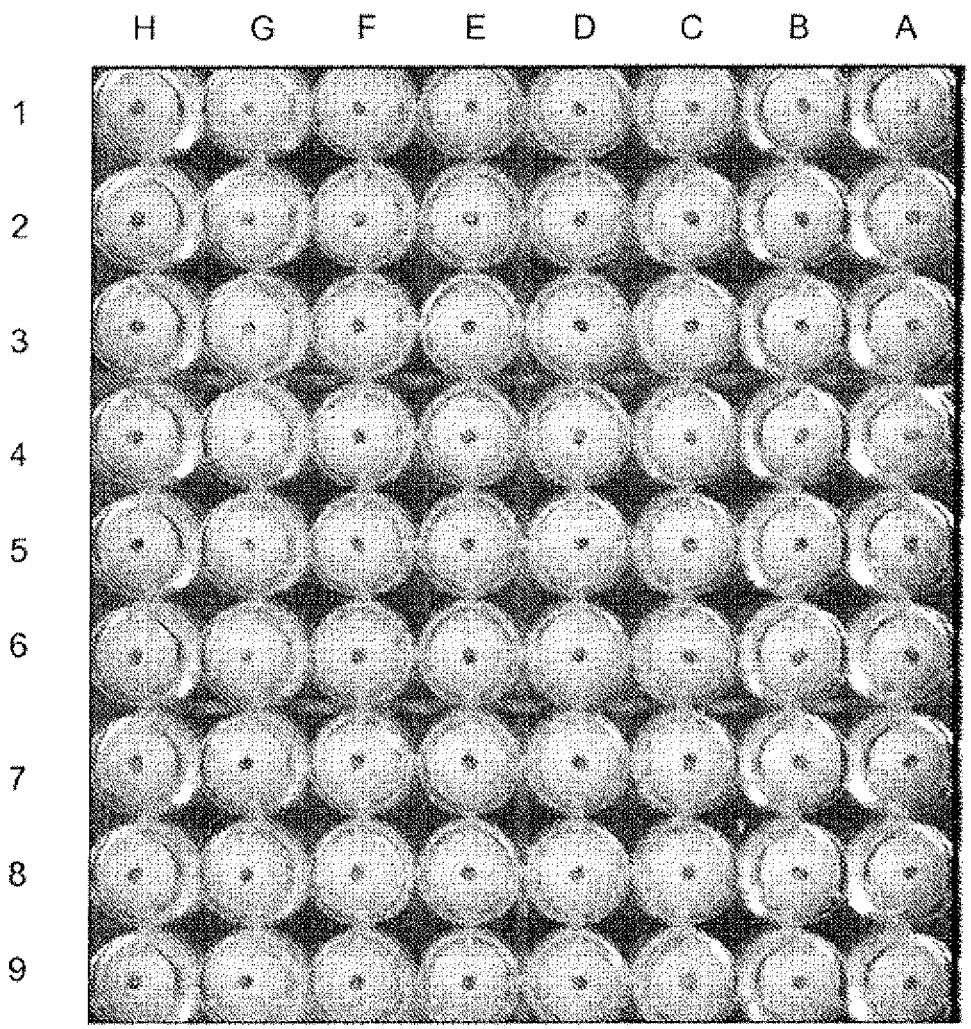
FIG. 6A represents a photograph of 9 strips of 8 wells indicated from 1 to 9 comprising *Staphylococcus aureus* CIP 76.25A bacteria (inoculated in the culture medium of the wells in columns B, C, D, E, F and G) comprising in the culture medium respectively ampicillin (line 1), ceftazidime (line 2), chloramphenicol (line 3), erythromycin (line 4), piperacillin (line 5), tetracycline (line 6), gentamicin (line 7), ciprofloxacin (line 8) or trimethoprim (line 9), as a function of the concentration: without antibiotics (column A=sterility control of the culture medium with magnetic particles, without bacteria, and column G=control of the culture medium with bacteria, with magnetic particles), 4 times the base concentration of the antibiotic (columns F and H), 2 times the base concentration of the antibiotic (column G), base concentration of the antibiotic (column D), 0.5 times the base concentration of the antibiotic (column C) or 0.25 times the base concentration of the antibiotic (column B) and magnetic particles before hydrodynamic action.
FIG. 6B represents the configuration from FIG. 6A but after hydrodynamic action.
Figure 6:
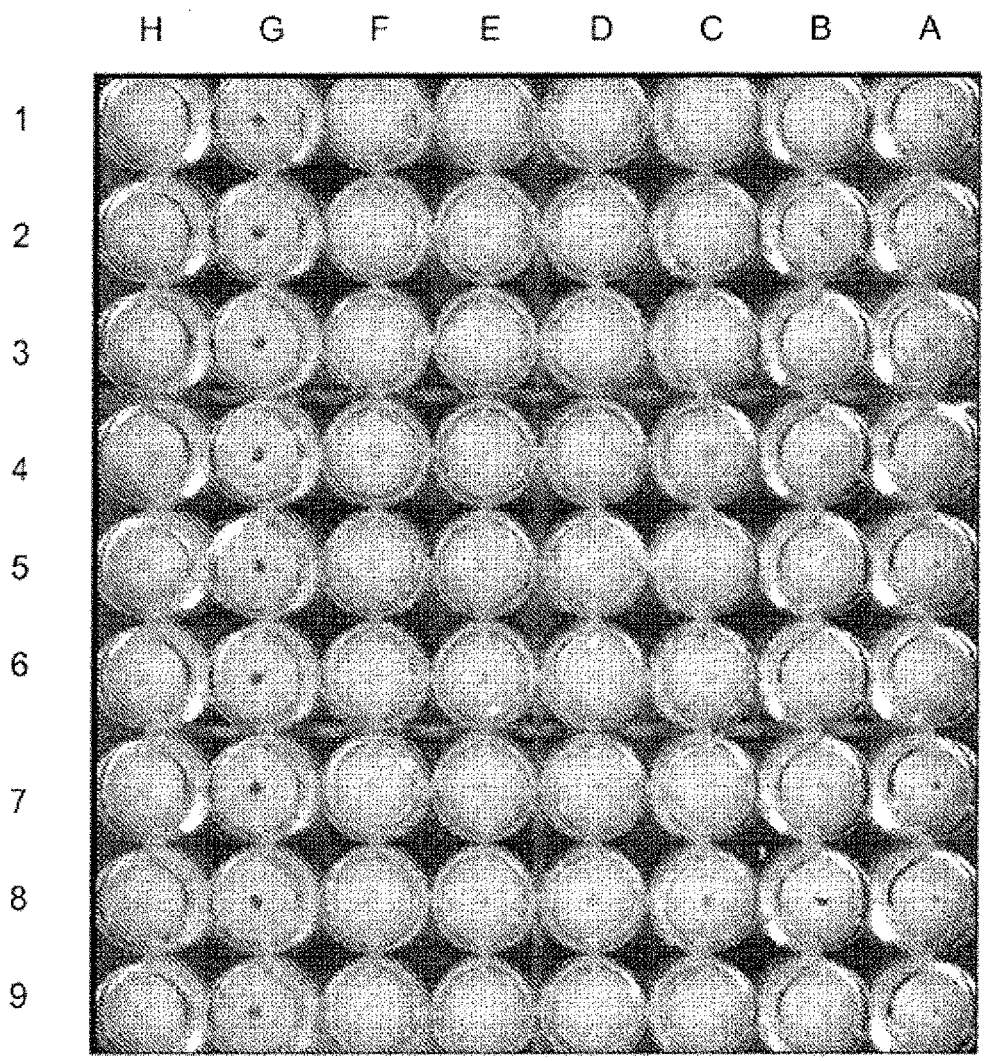

The final images obtained are represented in FIG. 6A. They were obtained by adding the red, green and blue components of the images of the red component of the color images obtained with the scanner using the ImageJ software (http://rsb.info.nih.gov.ij) and cutting out the images obtained with various adjustments of the contrast.

As represented in FIG. 6A, the spots are clearly defined and are visible in all the wells.

The strips were then placed on an orbital shaker (Variomag Monoshake, H+P Labortechnik, Germany) adjusted to 60%+/−20% of its maximum rotational speed for 10 seconds in order to subject them to a hydrodynamic action.

A second image acquisition was carried out under the same conditions as the first image and the final image obtained is represented in FIG. 6B.

As represented in FIG. 6B, spots and marks that are more or less clearly defined are visible, and their appearance depends on the antibiotic and on the concentration of antibiotic used.

As demonstrated in this example, the process of the invention makes it possible to determine the effect of an action, for example a hydrodynamic action, on a biofilm. In particular, the process of the invention makes it possible to determine the resistance of films relative to one another in the presence or absence of agents.

LIST OF REFERENCES

1. Physica Scripta., Vol. 65, 167-180 (2002): "Refractive Index Measurement and its Applications"

2. Voros et al., Biophysical Journal, Vol. 87, 553-561 (2004): "The Density and Refractive Index of Adsorbing Protein Layers"

The invention claimed is:

1. A process for determining the resistance of a film to an effect of an action comprising the following steps:
   a) introducing, into a solution present in a container, at least two particles, said particles resting on a submerged surface S in said solution,
   b) regrouping the particles on said submerged surface S, whereby said particles form on said surface a spot or a mark,
   c) introducing, into the solution, at least one substance capable of forming a film,
   d) forming a film from said at least one substance,
   e) observing the spot or mark on the surface S,
   f) applying a mechanical action to said container, and
   g) determining the effect of the action of step f) on the film by observing a change in the spot or mark on the surface S, wherein no change of the spot or mark indicates that the film is resistant to the effect of the action.

2. The process as claimed in claim 1, wherein the mechanical action applied to the container is selected from the group consisting of a reciprocating, a rotating, and a circular movement.

3. The process of claim 1 or 2, wherein the substance capable of forming a biofilm is chosen from microorganisms, foodstuffs and chemical substances.

4. The process of claim 3, wherein said, at least two, particles are independently a magnetic or magnetizable electrically charged particle or a particle covered with at least one magnetic or magnetizable layer.

5. The process of claim 3, further comprising illuminating the at least two particles by means of a light source in order to increase the contrast between the particle and the solution.

6. The process of claim 1 or 2, wherein said, at least two particles are independently a magnetic or magnetizable electrically charged particle or a particle covered with at least one magnetic or magnetizable layer.

7. The process of claim 1 or 2, further comprising illuminating the at least two particles by means of a light source in order to increase the contrast between the particle and the solution.

8. A process for determining the resistance of a film to an effect of an action comprising the following steps:
   a) introducing, into a solution, at least two particles, said particles resting on a submerged surface S in said solution,
   b) regrouping the particles on said submerged surface S, whereby said particles form on said surface a spot or a mark,
   c) introducing, into the solution, at least one substance capable of forming a film,
   d) forming a film from said at least one substance,
   e) observing the spot or mark on the surface S,
   f) applying to said solution a mechanical action,
      wherein said mechanical action is selected from the group consisting of: the application of a brush to the solution; and the application of a spatula to the solution, and
   g) determining the effect of the action of step f) on the film by observing a change in the spot or mark on the surface S, wherein no change of the spot or mark indicates that the film is resistant to the effect of the action.

9. The process of claim 8, wherein the substance capable of forming a biofilm is chosen from microorganisms, foodstuffs and chemical substances.

10. The process of claim 8, wherein said, at least two particles are independently a magnetic or magnetizable electrically charged particle or a particle covered with at least one magnetic or magnetizable layer.

11. The process of claim 8, further comprising illuminating the at least two particles by means of a light source in order to increase the contrast between the particle and the solution.

\* \* \* \* \*